United States Patent [19]

Oka et al.

[11] Patent Number: 4,696,796
[45] Date of Patent: Sep. 29, 1987

[54] MOISTURE SENSOR

[75] Inventors: Syotaro Oka, Muko; Shu Tahara, Nagaokakyo; Junya Kobayashi, Kyoto, all of Japan

[73] Assignee: Shimadzu Corporation, Kyoto, Japan

[21] Appl. No.: 772,562

[22] Filed: Sep. 4, 1985

[30] Foreign Application Priority Data

Sep. 8, 1984 [JP] Japan ............................ 59-188660

[51] Int. Cl.$^4$ ........................................... G01N 27/12
[52] U.S. Cl. ........................................ 422/88; 73/29; 73/336.5; 338/35; 422/98
[58] Field of Search ............... 422/98, 88; 436/151; 73/336.5, 29; 338/35

[56] References Cited

U.S. PATENT DOCUMENTS

| | | | |
|---|---|---|---|
| 2,728,831 | 12/1955 | Pope | 73/336.5 X |
| 3,559,456 | 2/1971 | Lomker | 73/336.5 X |
| 4,386,336 | 5/1983 | Kinomoto et al. | 73/336.5 X |
| 4,442,422 | 4/1984 | Murata et al. | 73/336.5 X |
| 4,520,341 | 5/1985 | Miyoshi et al. | 338/35 |
| 4,528,543 | 7/1985 | Miyoshi et al. | 338/35 |
| 4,562,725 | 1/1986 | Oka et al. | 73/336.5 X |

FOREIGN PATENT DOCUMENTS

| | | | |
|---|---|---|---|
| 0135946 | 8/1983 | Japan | 73/336.5 |
| 2138951 | 10/1984 | United Kingdom | 73/29 |
| 0543908 | 4/1977 | U.S.S.R. | 73/336.5 |

OTHER PUBLICATIONS

King, Jr., Research/Development, Apr. & May 1969, "Using Quartz Crystals as Sorption Detectors, Parts 1 & 2," pp. 28-34 in Apr. issue, pp. 28-33 in May issue.
Hijikigawa et al., Sensors & Actuators, 4(1983), 307-315.

Primary Examiner—Barry S. Richman
Assistant Examiner—Michael S. Gzybowski
Attorney, Agent, or Firm—Stiefel, Gross, Kurland & Pavane

[57] ABSTRACT

A moisture sensor having the moisture sensitive film comprising an inner layer in the form of a plasma-polymerized high polymer layer of a hydrophobic organic compound and a surface layer in the form of a plasma-polymerized high polymer layer having incorporated therein a hydrophilic groups of an ammonium salt type, and a process for producing same.

2 Claims, 9 Drawing Figures

MOISTURE SENSOR

BACKGROUND OF THE INVENTION

1. Field of the Invention

The present invention relates to a moisture sensor and a process for producing the same. More particularly, the invention relates to a moisture sensor which is useful for measuring the water content of various industrial process gases or recycle gases, for measuring the water content of high-pressure gases contained in cylinders, and for humidity measurements, and also to a process for producing the sensor.

2. Description of the Prior Art

Moisture sensors are already known which comprise a solid substrate of insulator, piezoelectric crystal, semiconductor or the like, having a moisture sensitive film formed on the substrate; a polyelectrolyte serving as the moisture sensitive substance.

Of these, the moisture sensor, wherein quartz crystal oscillator or like piezoelectric element is used as the substrate, determines the water content based on the variation of oscillation frequency of the piezoelectric element, serving as an indicator, which results from a change in the overal weight of the moisture sensitive film due to its hygroscopic action. Accordingly the sensor is capable of measuring water content . . . ppm lower than other types wherein variation of resistance or capacitance of the moisture sensitive film is used as an indicator. Such piezoelectric moisture sensors are usually produced by forming a pair of electrodes on the piezoelectric element and then coating the electrodes with a polyelectrolyte.

However, because the moisture sensitive film is formed by coating, the film is insufficietly adhered to the electrode surface and has poor durability. Further the sensor has low responsivity and stability when measuring very low water content in the ppm range. The moisture sensor further has difficulty in controlling the thickness of the moisture sensitive film.

A moisture sensor of the resistance type or capacitance type wherein a moisture sensitive film of polyelectrolyte is formed between a pair of electrodes on an insulator or semiconductor has similar problems with respect to the durability of the film, responsiveness, stability, etc.

We have already found that the above problems can be overcome by a piezoelectric moisture sensor which comprises a thin, high polymer film formed by plasma polymerization, having hydrophilic groups introduced into its surface layer, serving as the moisture sensitive film (U.S. patent application Ser. No. 516,959), now U.S. Pat. No. 4,567,725 granted Jan. 7, 1986.

The present invention, further developed from the above findings, provides a moisture sensor which comprises a moisture sensitive film consisting essentially of a plasma-polymerized high polymer layer and which has increased durability and improved responsiveness.

SUMMARY OF THE INVENTION

More specifically, the present invention provides a moisture sensor wherein a moisture sensitive film is formed on a solid substrate between or on at least one of a pair of electrodes. The moisture sensor is characterized in that the moisture sensitive film consists essentially of an inner layer in the form of a plasma-polymerized high polymer layer of a hydrophobic organic compound, and a surface layer provided over the inner layer in the form of an amino-containing high polymer layer of an organic amino compound formed by plasma polymerization, the amino-containing high polymer surface layer having incorporated therein hydrophilic groups of the ammonium salt type converted from amino groups.

The present invention further provides a process suited to the fabrication of the above moisture sensor.

DESCRIPTION OF THE PREFERRED EMBODIMENT

Figure 1:
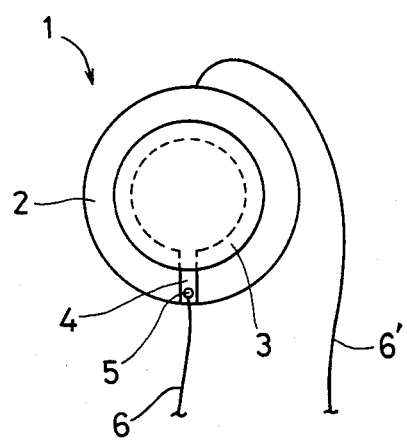
FIGS. 1 and 2 are a front view and a side elevation, respectively, showing a moisture sensor of the present invention for illustrative purposes.

The most distinct feature of the present invention is that the moisture sensitive film comprises a substantially hydrophobic inner layer and a surface layer having hydrophilic groups of the ammonium salt type and that each of these layers is in the form of a high polymer layer which is formed by plasma polymerization.

The inner layer of the moisture sensitive film of the present invention is formed by forming a pair of electrodes on a solid substrate for moisture sensors, and thereafter subjecting the electrode bearing substrate to plasma polymerization conditions in the vapor of a hydrophobic organic compound. Examples of useful hydrophobic organic compounds are various organic compounds having no hydrophilic groups, which include vinyl aromatic compounds such as styrene and divinylbenzene, aromatic hydrocarbons such as benzene and toluene, unsaturated hydrocarbons such as ethylene and propylene, etc. These compounds are used singly, or at least two of them are usable in combination. The inner layer can be of multi-layer structure. Of these compounds, it is desirable to use styrene which is amenable to plasma polymerization. Although the conditions for the plasma polymerization are not limited specifically, it is generally desirable to resort to glow discharge at 0.1 to 100 KHz in an atmosphere of the hydrophobic organic compound at 0.1 to 2 torr.

It is suitable that the inner layer thus formed be usually 0.01 to 10 μm in thickness. The formation of the layer is easily controllable to such a thickness by adjusting the plasma polymerization time. The inner layer of plasma-polymerized high polymer is crosslinked to a high degree, has strong adhesion to the underlying electrode or solid substrate and is a substantially hydrophobic polymer film of the hydrophobic organic compound. Accordingly, the layer serves as the base layer for the moisture sensitive film of the present invention.

The surface layer of the present moisture sensitive film is prepared by first subjecting the solid substrate coated with the inner layer to plasma polymerization conditions in the vapor of an organic amino compound to thereby form an amino-containing high polymer film over the inner layer, and subsequently treating the high polymer film chemically to thereby convert amino groups in the film to hydrophilic groups of the ammonium salt type. Examples of useful organic amino compounds are amines having at least one straight-chain substituent, such as diallylamine, diamylamine, diethylallylamine and N,N,N',N'-tetramethylhexanediamine, and cyclic or aromatic amines such as aniline, pyridine and phenethylamine. Also useful are triethylamine, ethylenediamine, diethylenetriamine, triethylenetetramine, etc. At least two of these amines may be used in combination. Of these compounds, it is preferable to use tertiary amines having a straight-chain substituent, such as tetramethylhexanediamine and diethylallylamine. For the plasma polymerization, it is preferred to resort to glow discharge which is generally conducted at 0.1 to 100 KHz in an atmosphere of the organic amino compound at 0.1 to 2 torr. It is suitable that the surface layer have a thickness of 0.1 to 10 $\mu$m. The thickness of the amino-containing high polymer film can be controlled by adjusting the plasma polymerization time.

The high polymer film formed over the inner layer by the plasma polymerization of the organic amino compound is an amino-containing high polymer film having a high cross-linking degree and is united with the hydrophobic high polymer inner layer by being chemically bonded thereto, for example, by radical formation resulting from the glow discharge. All the amino groups of the organic amino monomer do not always remain in the chain of the high polymer film formed by the plasma polymerization. Under the foregoing conditions for the plasma polymerization of organic amino compound, a random polymerization-crosslinking reaction between carbon chains (substituents) appears predominant owing to the formation of many radicals and ions, whereas other reactions such as decomposition of amino groups will also take place.

In this connection, we have obtained the interesting finding that the high polymer film resulting from the plasma polymerization of the organic amino compound has a higher amino content toward its front side and a lower amino content toward its rear side. Such a gradient of amino content is distinct when organic amino compounds with a straight-chain substituent are used. It is believed that the gradient is related to the responsiveness of the moisture sensor of the invention, especially to the effect of rapidly adsorbing and desorbing water.

The amino groups present in the amino-containing high polymer film are chemically treated preferably by holding the substrate formed with the film in the vapor of an alkyl halide. Suitable alkyl halides are monohalogenated lower alkyls, which include, for example, methyl chloride, ethyl chloride, methyl iodide, methyl bromide, etc. When the high polymer film is brought into contact with the vapor of such alkyl halide, amino groups present therein are alkylated into hydrophilic groups of the ammonium salt type, such as quaternary ammonium salt, tertiary amine salt, secondary amine salt type or the like. While the conversion reaction can be accelerated by effecting the contact at an elevated temperature, the reaction can be carried out at room temperature. The akyl halide vapor is supplied preferably at a flow rate of about 1 liter/minute at atmospheric pressure for contact with the sensor having the amino-containing high polymer film formed thereon. It is suitable that the contact (retention) time be usually about 30 to about 300 minutes, although the contact time is dependent on the desired thickness of the surface layer.

The solid substrate on which the moisture sensitive film comprising an inner layer and an outer layer is to be formed is selected according to the detection system contemplated. For example, when variation of electrical resistance or capacitance serves as an indicator for the contemplated moisture sensor, an insulator or semiconductor is used as the solid substrate, and the moisture sensitive film is formed between, and further over, a pair of electrodes, preferably comb-shaped electrodes, provided on one surface of the substrate. Preferably, the present invention is embodied as a piezoelectric moisture sensor which comprises a piezoelectric element serving as the solid substrate, a pair of electrodes formed on the opposite sides of the element individually, and a moisture sensitive film formed over at least one of the electrodes. Partly because of the measuring system used, the sensor is capable of measuring water content of as low as several ppm with good stability over a prolonged period of time. Examples of useful piezoelectric elements are quartz crystal oscillator, achroite, Rochelle salt, barium titanate crystal, zinc oxide crystal, etc. Of these, a quartz crystal oscillator in the form of a flat plate is especially preferable. A thin film of gold, silver or like noble metal is used as the electrode on the solid substrate. The electrode is formed by vacuum evaporation.

As described above, the moisture sensor of the present invention comprises a moisture sensitive film which is composed of a substantially hydrophobic high polymer film (inner layer) formed by plasma polymerization, and a plasma-polymerized high polymer film (surface layer) formed over the inner layer integrally therewith and having incorporated therein hydrophilic groups of the ammonium salt type. Accordingly, the surface layer only adsorbs and desorbs water, without substantially permitting water to penetrate or migrate into the inner layer. Further because the concentration of hydrophilic groups incorporated in the surface layer is highest at the surface of the layer and decreases toward the inner layer, water can be adsorbed and desorbed smoothly. This minimizes adverse effects such as delayed response due to the presence of remaining water in the moisture sensitive film. Accordingly, the moisture sensor of the present invention is outstanding in responsiveness and stability and has improved durability.

EXAMPLE 1

A gold electrode, 8 mm in diameter and about 1 $\mu$m in thickness, was formed by vacuum evaporation at the center of a disk-like quartz crystal oscillator 2, 14 mm in diameter and 0.2 mm in thickness, on each surface thereof. The oscillator was about 9.03 MHz in oscillation frequency.

Figure 4:
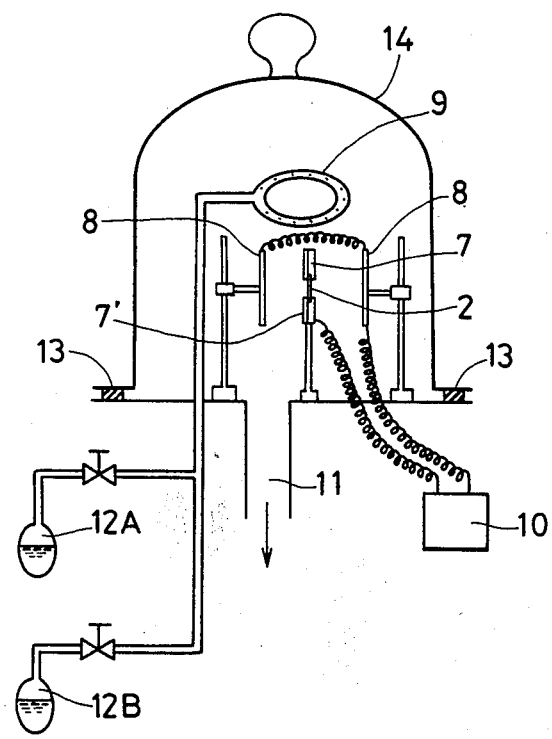
FIG. 4 is a diagram showing a plasma polymerization apparatus for use in producing the moisture sensor of the present invention.

The oscillator 2 was set in a plasma polymerization apparatus as shown in FIG. 4. With reference to this diagram, indicated at 7 is an aluminum discharge electrode, at 8 a similar counter-electrode, at 9 a compound supply nozzle member, at 10 an R.F. power supply, at 11 a pipe connected to a vacuum pump, at 12A a container for a hydrophobic organic compound, i.e. styrene monomer, at 12B a container for an organic amino compound, i.e. N,N,N',N'-tetramethylhexanediamine, at 13 a seal, and at 14 a sealed container. The oscillator 2 was masked at its peripheral portion with an aluminum holder plate 7' so that a plasma-polymerized thin film, 12 mm in diameter, was formed over each circular gold electrode provided on the oscillator in intimate contact therewith.

Subsequently, the interior of the container 14 was evacuated by the vacuum pump to a vacuum of up to 0.01 torr. With the vapor of styrene monomer introduced into the container to a pressure of 1 torr, plasma polymerization was conducted under the following conditions for 20 seconds, whereby a thin polystyrene film, about 3000 angstroms in thickness, was formed over each gold electrode concentrically with the electrode in intimate contact therewith.

Discharge conditions
Temperature: 25° C.
Discharge frequency: 1 KHz.
Discharge power: 3.5 W.

Next, the interior of the container was evacuated to 0.01 torr, the vapor of N,N,N',N'-tetramethylhexanediamine was supplied to a pressure of 1 torr, and plasma polymerization was conducted for 60 seconds under the same conditions as above, whereby an amino-containing high polymer film, about 5000 angstroms in thickness, was formed over the polystyrene film in intimate contact therewith.

The quartz crystal oscillator thus coated by plasma polymerization was allowed to stand for 12 hours in a container containing methyl chloride vapor (closed container of atmospheric pressure with 100% methyl chloride gas introduced therein), whereby amino groups present in the amino-containing high polymer film (surface layer) were alkylated into hydrophilic groups of the ammonium salt type.

Figure 2:
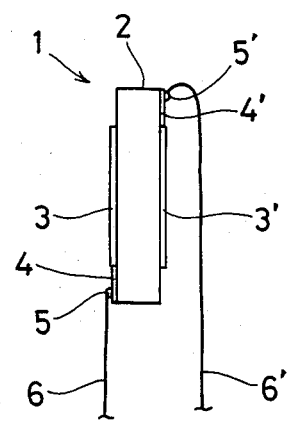
Figure 3:
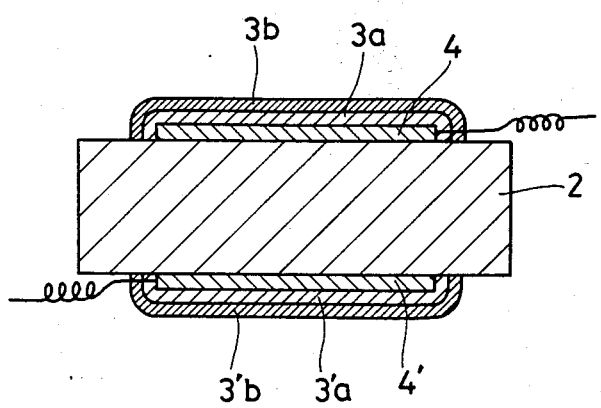
FIG. 3 is a view illustrating the construction of the moisture sensor.

FIGS. 1 to 3 show the moisture sensor thus obtained according to the present invention. With reference to these drawings, the sensor 1 comprises gold electrodes 4, 4' formed on the opposite surfaces of the quartz crystal oscillator 2 in intimate contact therewith, and moisture sensitive films 3, 3' formed over the electrodes 4, 4', respectively, in intimate contact therewith. End portions of the gold electrodes 4, 4' are connected via terminals 5, 5= to lead wires 6, 6', which are connected to an oscillator circuit when the sensor is to be used. Each of the moisture sensitive films 3, 3' comprises a plasma-polymerized polystyrene film 3a (3'a) in intimate contact with the gold electrode and with the oscillator, and a plasma-polymerized high polymer film 3b (3'b) containing hydrophilic groups of the ammonium salt type and formed over the polystrene film. When to be used for a gas, the sensor is positioned with the moisture sensitive films 3, 3' exposed to the gas, and the water content of the gas can be measured based on the variation of frequency of the quartz crystal oscillator.

The moisture sensor thus prepared was fixedly provided within a container having a specimen gas inlet tube and an outlet for measuring water content. The results are given below in comparison with those achieved by a conventional moisture sensor.

(1) Responsiveness in N₂ having a water concentration of 500 to 10,000 ppm

Figure 5:
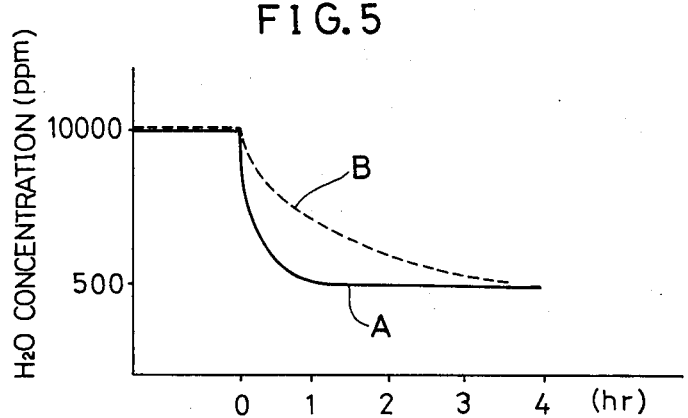
FIGS. 5 and 6 are graphs each showing the moisture responsiveness of the sensor of the invention in comparison with that of a conventional sensor.

The responsiveness of the moisture sensor was evaluated by introducing an N₂ gas containing 10,000 ppm of water into the container for 10 minutes, measuring the output of the sensor due to the adsorption of water, thereafter introducing an N₂ gas with a water content of 500 ppm and measuring the resulting change in the output. The result is shown in FIG. 5, in which indicated at A is the change in the output of the moisture sensor of the invention, and at B that of the conventional moisture sensor, which was prepared in the same manner as above except that the moisture sensitive layer consisted singly of a plasma-polymerized polystyrene film having sulfonate groups incorporated in the surface layer of the film and serving as hydrophilic groups.

It is seen that the moisture sensor A of the present invention reached a steady state in about 0.5 hour in response to the abrupt moisture content change from 10,000 ppm to 500 ppm within the region of relatively high concentrations and is therefore exceedingly superior in responsiveness to the conventional sensor B which required about 4 hours to reach a steady state.

(2) Responsiveness to a water concentration of 0 to 5 ppm

Figure 6:
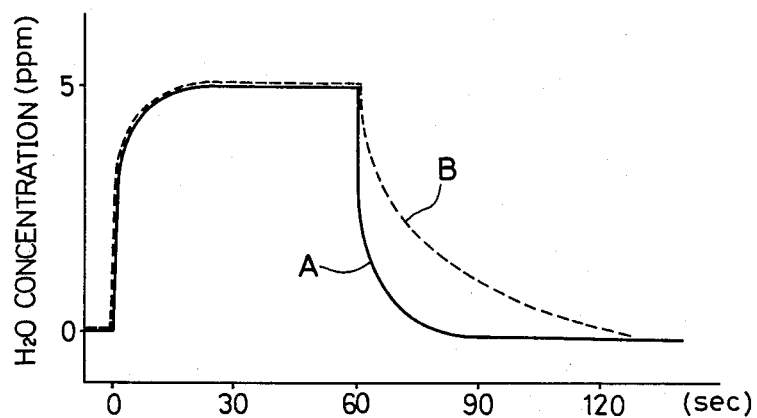

The responsiveness was similarly evaluated by measuring the variation of output resulting from changes in moisture content (0→5→0 ppm) in the region of very low concentrations. FIG. 6 shows the result.

The graph reveals that the sensor A of the invention has extremely high responsiveness to the moisture content changes in the low concentration region, compared to the conventional sensor B especially to the reduction of moisture content.

(3) Durability of the moisture sensitive film

Figure 7:
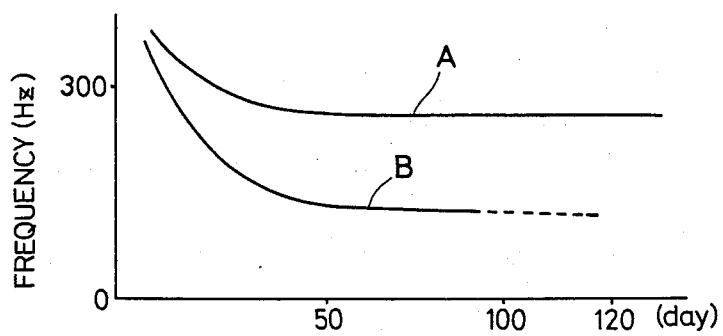
FIG. 7 is a graph showing the durability of the present sensor in comparison with that of the conventional sensor.

The durability of the moisture sensitive film was evaluated by using the sensor for continuous measurement over a prolonged period of time of N₂ gas containing 1000 ppm of water and tracing the resulting variation of the output. FIG. 7 shows the result. The conventional sensor B initially exhibited a marked reduction in sensitivity and developed a change in the quality of the film in 90 days (indicated in the broken line), whereas the sensor of the present invention was small in initial sensitivity reduction and was found free of any change in the film even after 120 days.

EXAMPLE 2

A moisture sensitive film of double layer structure was prepared in the same manner as in Example 1 except that methyl iodide was used as the alkyl halide. Another moisture sensitive film was prepared in the same manner as in Example 1 with the exception of using aniline in place of N,N,N',N'-tetramethylhexanediamine and using methyl iodide as the alkyl halide. Measurements were made of the distribution of ammonium groups in the surface layers of these films by ESCA and Ar etching. The conditions for ESCA analysis were as follows.

Figure 8:
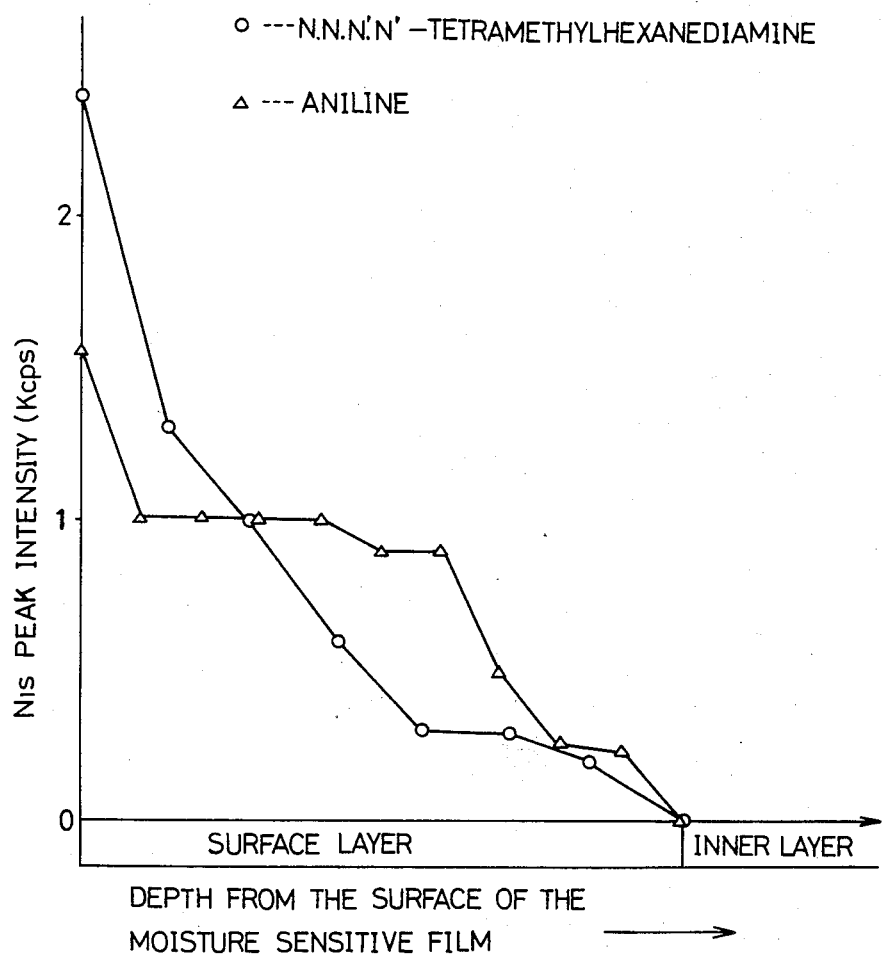
FIG. 8 is a graph showing the distribution of nitrogen atoms in the high polymer amino-containing surface layer in the direction of thickness thereof, as determined for the moisture sensitive films of sensors of the invention for illustrative purposes.

X-ray source: 9 KV, 30 mA, Mg target
Scanning speeds: 1 eV/sec and 0.1 eV/sec
Ar etching: 2 KV, 20 mA FIG. 8 shows the relationship between the film thickness and $N_{1s}$ peak intensity as established by the results of measurements.

The graph shows that the surface layer contains ammonium groups with a greater gradient from its surface inward when prepared from an amine monomer having a straight-chain substituent, such as tetramethylhexanediamine than when prepared from an aromatic amine, such as aniline, and that the ammonium content is highest at the outermost surface portion of the layer. The use of amines of the former type is therefore desirable to assure rapid adsorption and desorption of water.

EXAMPLE 3

Figure 9:
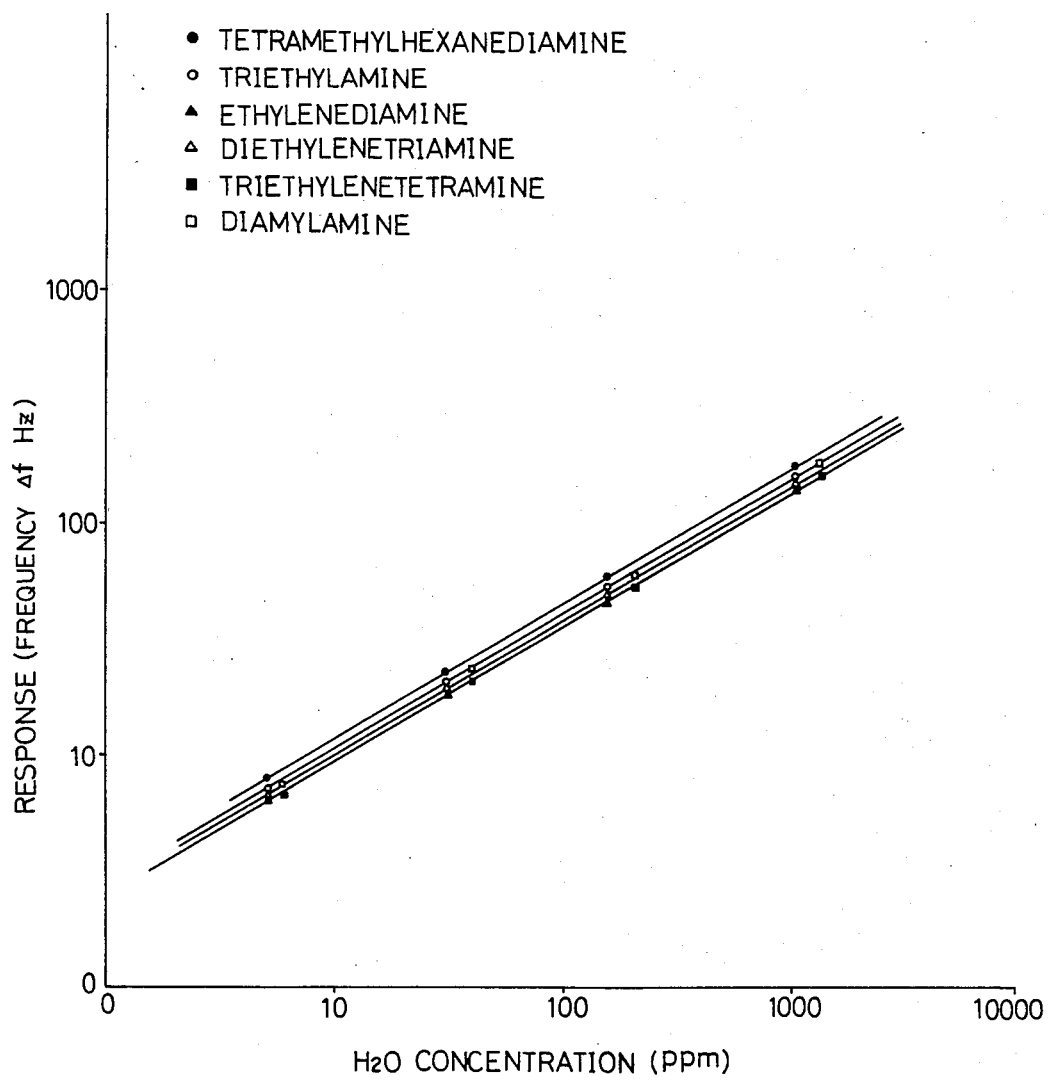
FIG. 9 is a graph showing the responsiveness of moisture sensors of the invention wherein different organic amino compounds are used.

Piezoelectric moisture sensors were prepared in the same manner as in Example 1 using various organic amino compounds (triethylamine, ethylenediamine, diethylenetriamine, triethylenetetramine and diamylamine). The sensors were tested for responsiveness to water contents. FIG. 9 shows the results.

As described above, the moisture sensor of the present invention is superior in responsiveness and durability to the moisture sensor in which a plasma-polymerized high polymer film in the form of a single layer serves as the base of the moisture sensitive film. As compared with conventional sensors wherein the film is formed by coating, the present sensor is superior in responsiveness and durability, assures greater ease of film thickness control and more facilitated quality control and, moreover, can be produced by a more convenient and economical procedure without losses because the entire production process is practiced under a dry condition with use of commercially available gases.

What we claim is:
1. A moisture sensor comprising:
 (a) a solid substrate comprising a piezoelectric element;
 (b) a pair of electrodes formed on said substrate; and
 (c) a moisture sensitive film formed on at least one of said electrodes, said film comprising:
  an inner, plasma-polymerized, highly crosslinked high polymer layer of a hydrophobic organic compound, and
  an outer surface layer chemically bonded to said inner layer, said outer surface layer comprising an amino-containing highly crosslinked high polymer layer of an organic amino compound formed by plasma polymerization, said outer surface layer having incorporated therein a concentration gradient of ammonium salt-containing hydrophilic groups, decreasing from an exposed surface of said surface layer to said inner layer.
2. The moisture sensor of claim 1, wherein the piezoelectric element is selected from the group consisting of quartz crystal oscillators, achroite, Rochelle salts, barium titanate crystals, and a zinc oxide crystals.

* * * * *